US012796896B2

(12) United States Patent
Kuan et al.

(10) Patent No.: US 12,796,896 B2
(45) Date of Patent: Nov. 17, 2026

(54) APPARATUS FOR CAPSULE RETRIEVAL PAN

(71) Applicant: CAPSOVISION, Inc., Saratoga, CA (US)

(72) Inventors: Shu Hsuan Kuan, Taipei (TW); Ganyu Lu, Palo Alto, CA (US); Kang-Huai Wang, Saratoga, CA (US); Gordon C. Wilson, San Francisco, CA (US)

( * ) Notice: Subject to any disclaimer, the term of this patent is extended or adjusted under 35 U.S.C. 154(b) by 490 days.

(21) Appl. No.: 18/036,161

(22) PCT Filed: Nov. 18, 2021

(86) PCT No.: PCT/US2021/059868
§ 371 (c)(1),
(2) Date: May 9, 2023

(87) PCT Pub. No.: WO2022/115306
PCT Pub. Date: Jun. 2, 2022

(65) Prior Publication Data

US 2023/0414074 A1 Dec. 28, 2023

Related U.S. Application Data

(60) Provisional application No. 63/117,721, filed on Nov. 24, 2020.

(51) Int. Cl.
*A61B 1/00* (2006.01)
*E03D 11/13* (2006.01)

(52) U.S. Cl.
CPC .......... *A61B 1/00131* (2013.01); *E03D 11/13* (2013.01)

(58) Field of Classification Search
CPC ............................ A61B 1/00131; E03D 11/13
See application file for complete search history.

(56) References Cited

U.S. PATENT DOCUMENTS 4,445,235 A 5/1984 Slover et al.
2014/0017720 A1* 1/2014 Sidorsky ............ B01D 11/0292 435/309.1

FOREIGN PATENT DOCUMENTS

WO WO-2020111959 A1 * 6/2020 ......... A61B 10/0038
WO WO 2020/225575 A2 11/2020

* cited by examiner

*Primary Examiner* — Charles Capozzi
*Assistant Examiner* — Alex Ramirez
(74) *Attorney, Agent, or Firm* — Blairtech Solution LLC

(57) ABSTRACT

The present invention discloses a device for retrieving a medical capsule. The collection pan comprises a flange to adapt to a rim of the toilet bowl and a collection cup joined to the flange around the capture opening. The flange comprises a capture opening for collecting feces, and two wings of the flange extended from the capture opening are placed over the rim of the toilet bowl to support the collection pan. The collection cup comprises a cup wall and a sifting part at bottom of the collection cup. The sifting part comprises a plurality of holes to allow liquied or soft feces to pass while preventing the capsule to pass. The flange and the collection cup are made of rubber or rubber-alike materials. The flange is flexible to fold down and to bend up. The cup wall is flexible to collapse and to extend from collapsed state.

13 Claims, 8 Drawing Sheets

APPARATUS FOR CAPSULE RETRIEVAL PAN

CROSS REFERENCE TO RELATED APPLICATIONS

The present invention claims priority to U.S. Provisional Patent application, No. 63/117,721, filed Nov. 24, 2020. The present invention is related to U.S. patent application, published as US20120101481A1, on Apr. 26, 2012. The U.S. Provisional patent application and the Non-Provisional patent application are hereby incorporated by reference in their entireties.

FIELD OF THE INVENTION

The present invention relates to medical capsule inside a human body. In particular, the present invention relates to retrieving the capsule upon its exiting from the human body.

BACKGROUND

Medical capsules have been widely used for monitoring and diagnostic purposes. The capsule is swallowed by a patient and travels through the tract of the human body. When the capsule travels in the tract, it performs monitoring and/or diagnostic tasks such as measuring temperature and pH values, and capturing images. The measured or captured data may be transmitted to a device outside the body using wireless transmission or using the body as a transmission medium. Alternatively, the measured or captured data may be stored in a storage device within the capsule. The stored data can be recovered from the capsule after it exits from the body. In the latter case, there is a need for retrieving the capsule. Even for the capsule without on-board storage, there may still be a need for retrieving the capsule so that the capsule may be reused, or to prevent obstruction of the plumbing, or to comply with local laws governing disposal and recycling of devices containing batteries or other regulated components or materials.

When the capsule exits from the anus of a patient, it is often mixed with feces, where the feces include all excretions such as digested and partially-digested food, water, other liquids, and bile. It is desirable to design a cost effective, easy-to-deploy, and comfortable-to-use device that can be used to retrieve the capsule.

BRIEF SUMMARY OF THE INVENTION

The present invention discloses a device for retrieving a medical capsule. The collection pan for retrieving a capsule discharged from anus of a patient into a bowl comprises a flange to adapt to a rim of the toilet bowl and a collection cup joined to the flange around the capture opening. The flange comprises a capture opening for collecting feces, the flange is longer in one direction than the other, and two wings of the flange extended from the capture opening in a long direction are placed over the rim of the toilet bowl to support the collection pan. The collection cup comprises a cup wall and a sifting part at bottom of the collection cup, and the sifting part comprises a plurality of holes to allow liquid or soft feces to pass while preventing the capsule to pass. The flange and the collection cup are made of rubber or rubber-alike materials. The flange is flexible to fold down and to bend up. The cup wall is flexible to collapse under pressure applied to top of the collection cup and the bottom of the collection cup and to extend from collapsed state when a pull force is applied to the bottom of the collection cup.

In one embodiment, the flange and the collection cup are made of a same material.

In one embodiment, the flange comprises at least one bump on each of the two wings of the flange and distance between corresponding bumps of the two wings matches rim dimension of typical toilets. In one embodiment, the height of the bumps including thickness of the flange is between 4 mm to 12 mm.

In one embodiment, the flange has a thickness between 1 mm and 6 mm. In one embodiment, the flange has a length between 200 mm and 500 mm. In one embodiment, the flange has a width between 40 mm and 400 mm.

In one embodiment, the cup wall has a thickness between 0.2 mm and 4 mm. Furthermore, the cup wall may comprise one or more folding lines.

In one embodiment, the plurality of holes has a shape of round, square, rectangle or triangular. In one embodiment, the plurality of holes is round with a diameter between 0.2 mm and 12 mm.

In one embodiment, the capture opening is round with a diameter between 40 mm and 400 mm.

In one embodiment, the height of the collection cup at a fully extended state is between 10 mm and 300 mm.

BRIEF DESCRIPTION OF THE DRAWINGS

FIG. 4A shows the pan in a state with the flange and the collapsible cup fully extended, FIG. 4B shows the pan in a state with the flange folded and the collapsible cup collapsed, and FIG. 4C shows the pan in a state with the flange expanded and the collapsible cup collapsed.

DETAILED DESCRIPTION OF THE INVENTION

Medical capsules have been widely used for monitoring and diagnostic purposes.

The capsule is administered by swallowing it by a patient and the capsule travels through the gastrointestinal (GI) tract of the human body. When the capsule travels in the tract, it performs its monitoring and diagnostic tasks such as measuring temperature and pH values, and capturing images. The measured or captured data may be transmitted to a device outside the body using wireless transmission or using the body as a transmission medium. Alternatively, the measured or captured data may be stored in an on-board storage device inside the capsule. The stored data can be recovered from the capsule after it exits from the human body. In the latter case, there is a need for retrieving the capsule. Nevertheless, even for capsules without on-board storage, there may still be benefits for retrieving the capsules so that the capsules may be recovered for reuse to save cost.

Figure 1:
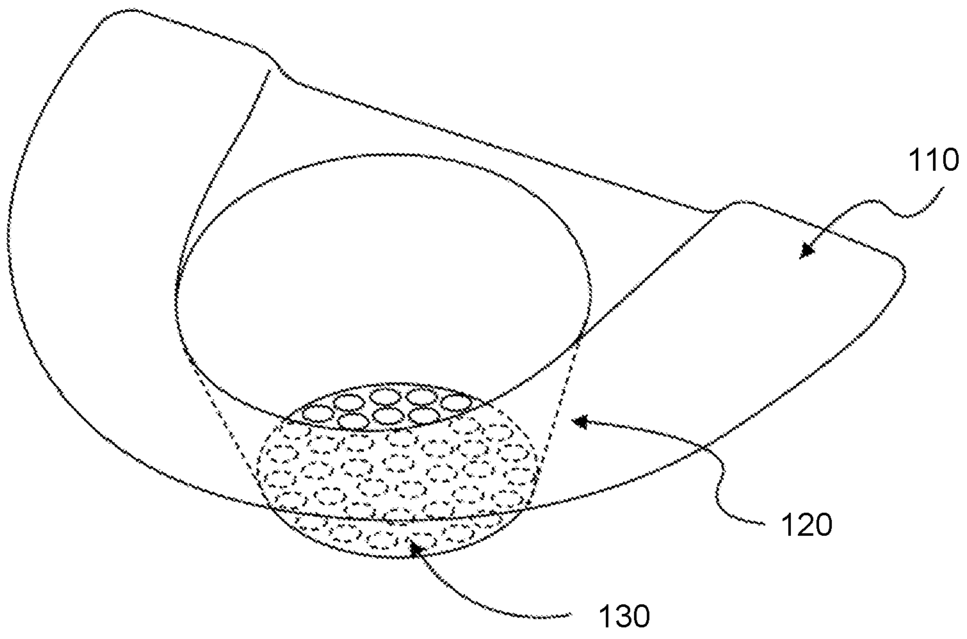
FIG. 1 illustrates a capture device converted from an off-the-shelf capture device of for retrieving a capsule discharged from the anus of a patient.

A retrieval kit that can easily separate the capsule from the feces and can easily pick up the capsule has been disclosed in U.S. patent application, published as US20120101481A1, on Apr. 26, 2012. For example, a retrieval kit is disclosed in US20120101481A1 as shown in FIG. 1, where the retrieval kit comprises two parts: a capture device 100 and a wand 150. The capture device 100 comprises a flange 110 to be adapted to a toilet bowl by placing the flange 110 over the rim of the toilet bowl. The bottom of the capture device is a sifting piece 130 which contains openings large enough to allow feces to pass through and small enough to prevent the capsule from passing through. The wall 120 is a structure to connect the flange and the sifting piece and keeping the capsule on the sifting piece 130. While a solid wall is shown in FIG. 1, the wall 120 can also be made of any flexible or solid material that is strong enough to connect the sifting piece 130 to the flange 110. The wall may also contain openings to allow liquid or feces to overflow or to reduce weight of the capture device. When the wall 120 contains openings, the opening should be small enough to prevent capsule from passing through.

Figure 2A:
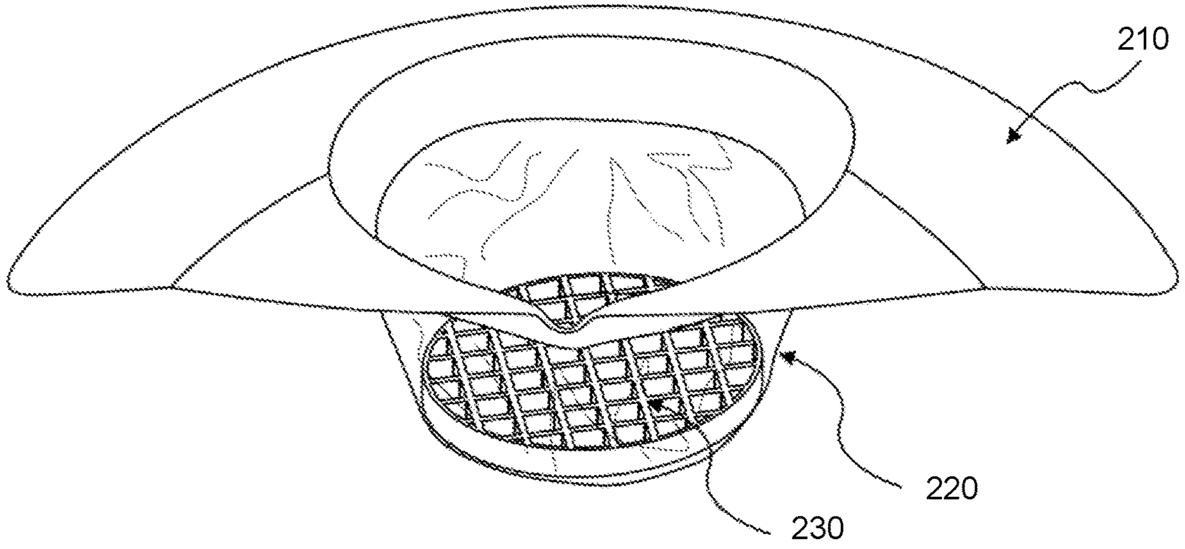
FIG. 2A illustrates another collapsible capture device for retrieving a capsule discharged from the anus of a patient.
Figure 2B:
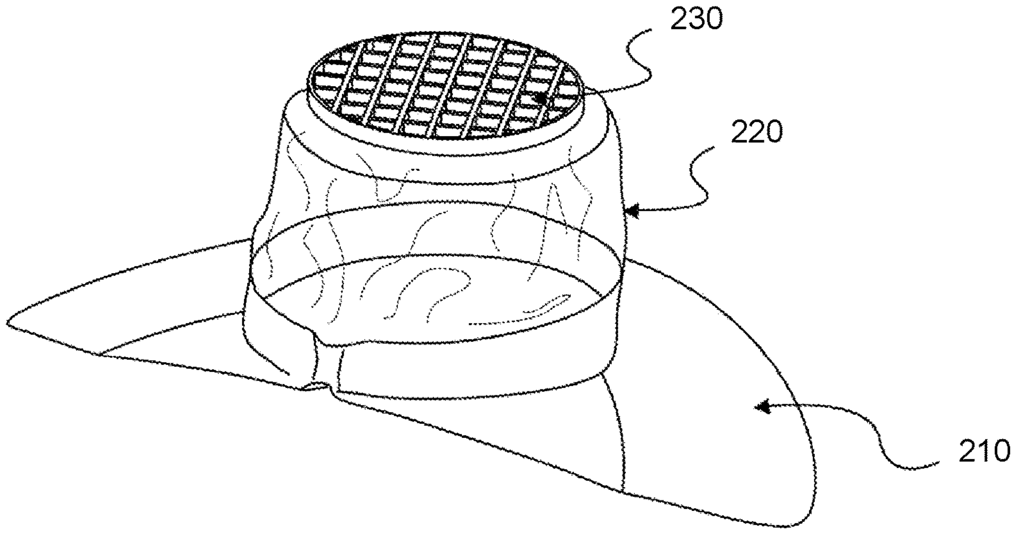
FIG. 2B illustrates a bottom view of the collapsible capture device in FIG. 2A.
Figure 2C:
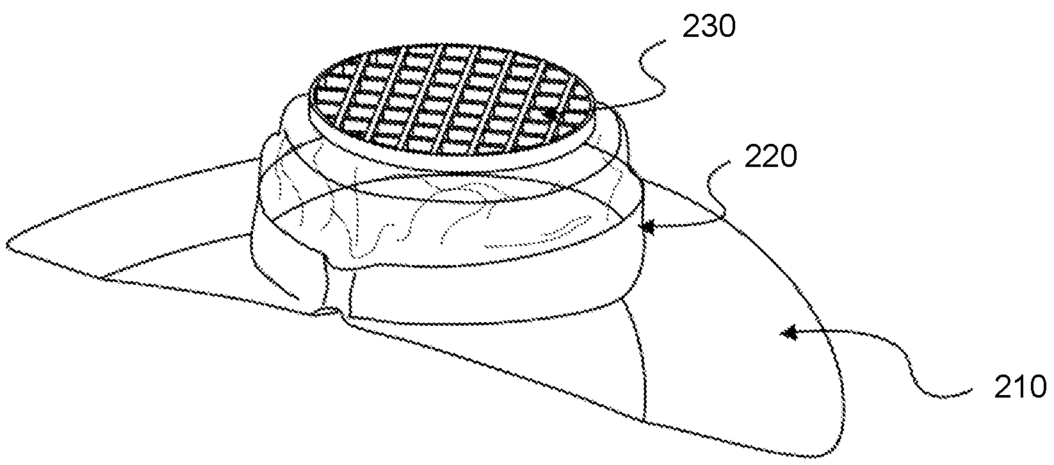
FIG. 2C illustrates the collapsible capture device in FIG. 2A in a partially collapsed position.
Figure 2D:
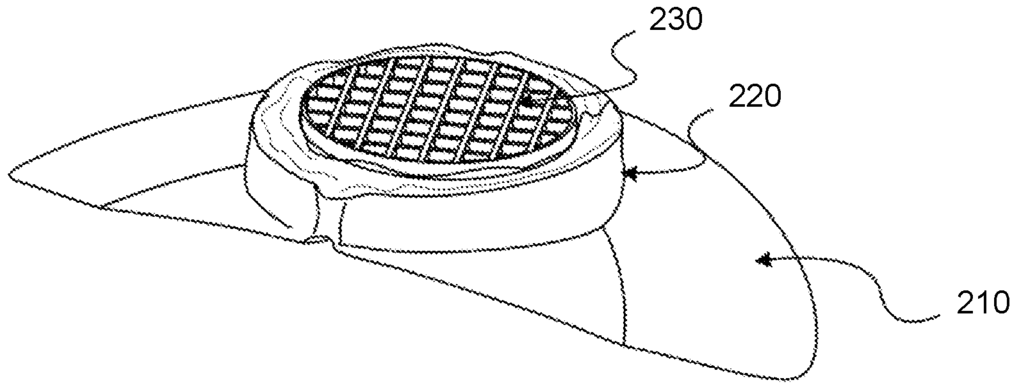
FIG. 2D illustrates the collapsible capture device in FIG. 2A in a fully collapsed position.

The retrieval kit in FIG. 1 has a solid wall, which is rather large for storage or shipping. In order to save space, a collapsible retrieval device has also been disclosed in US20120101481A1 as shown in FIG. 2A-FIG. 2D. FIG. 2A illustrates the collapsible capture device 200 in the upright position. The capture device 200 comprises a flange 210, a flexible wall 220 and a sifting piece 230. The collapsible capture device is shown in an upside down position in FIG. 2B. The material for the wall shown in FIG. 2A-FIG. 2D is made of flexible plastic sheet and the wall 220 can be collapsed by pushing the sifting piece 230 down when the collapsible capture device is in an upside down position or pushing the flange 210 down when the collapsible capture device is in an upright position. The wall 220 is shown in a partially collapsed position in FIG. 2C and fully collapsed in FIG. 2D. The wall may also be made of other flexible materials such as mesh fabric or soft cloth. When the flexible wall is made of a material substantially soft, the collapsible capture device may collapse by itself due to gravity. The sifting piece 230 shown in FIG. 2A-FIG. 2D is made of grate where the opening size is large enough for feces to pass through easily while small enough to retain the capsule. Other materials that contain openings of proper size and sturdy enough to sustain feces and liquid passing through it can also be used for sifting piece. For example, holes can be punched or drilled on a flat sheet of metal, plastic, cardboard, or other rigid material to make the material suitable for sifting piece. A material having the honeycomb structure can also be used as a material for the sifting piece as long as the opening size is large enough to pass the feces and small enough to retain the capsule. FIG. 2D illustrates a collapsible capture device in a fully collapsed position.

Figure 3A:
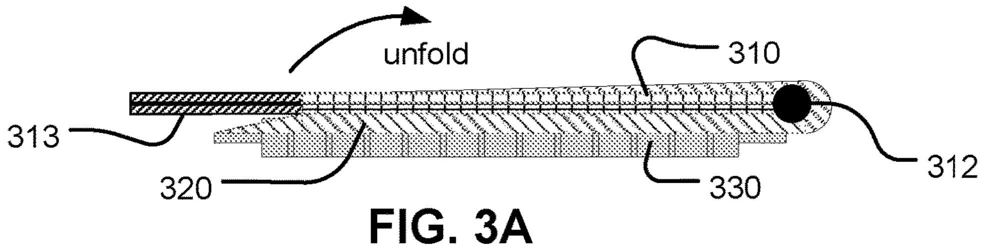
FIG. 3A illustrates a foldable capture device for retrieving a capsule discharged from the anus of a patient, where the device is shown in a folded position.
Figure 3B:
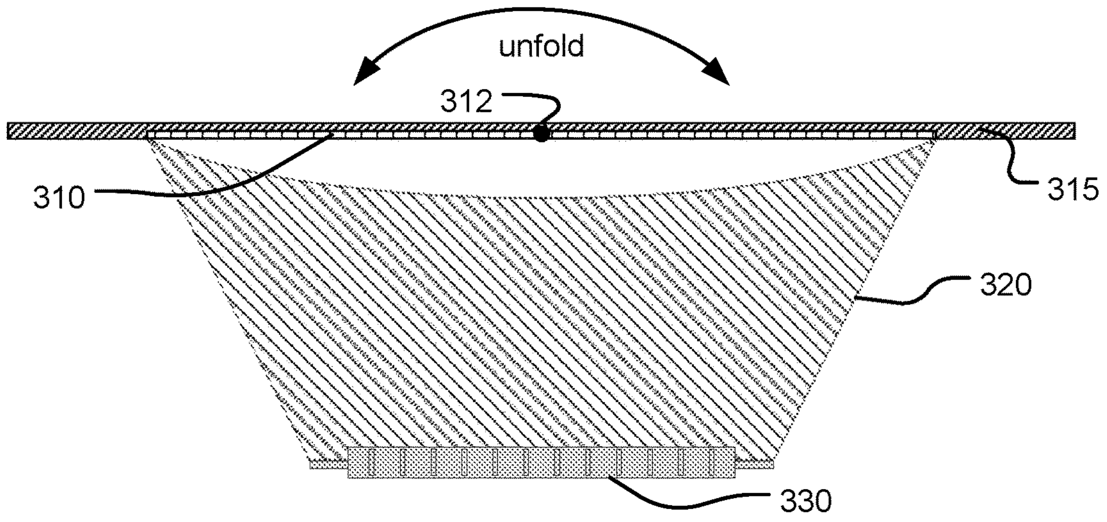
FIG. 3B illustrates the foldable capture device in FIG. 3A in an unfolded position.
Figure 3C:
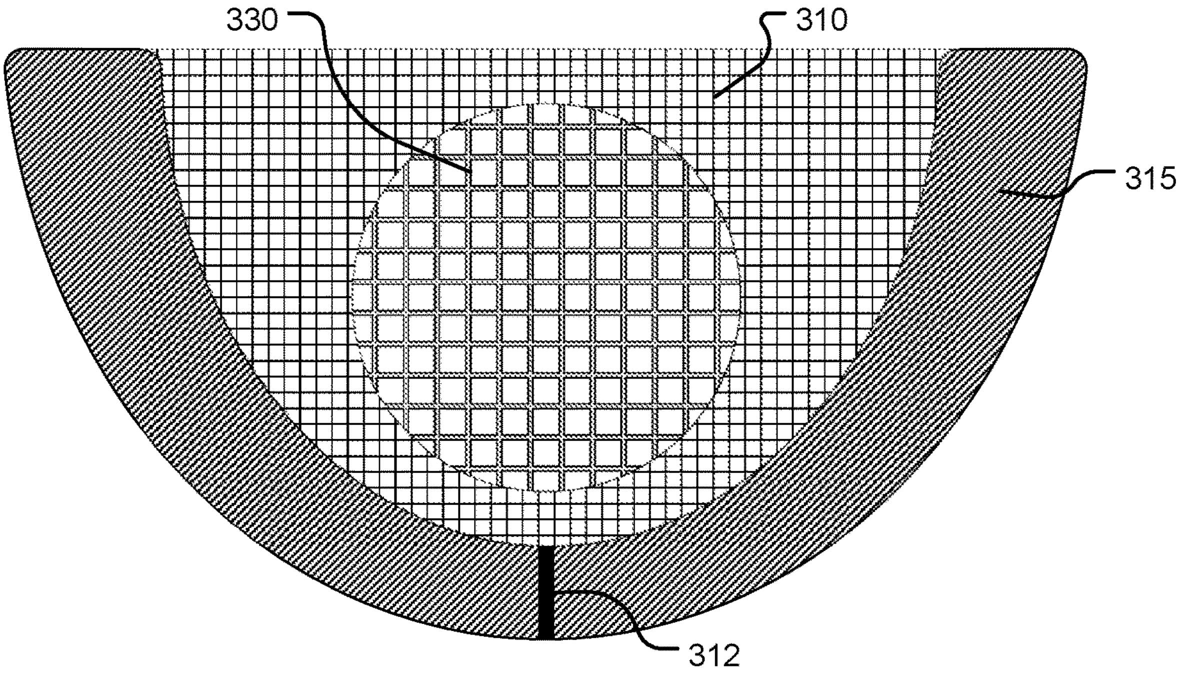
FIG. 3C illustrates a top view of the foldable capture device of FIG. 3B.

While the capture device conserves the vertical space, the flange 230 may still take up quite sizeable horizontal space. In order to further improve the compactness of the capture device for shipment, a capture device embodying the present invention comprises a foldable flange. A collapsible and foldable capture device 300 is shown in FIG. 3A in a collapsed and folded position. The flange 310 is made of flexible materials for easy folding. The flange contains a frame 315 having two sides joined by a locking hinge 312. The frame 315 is rigid to keep the flexible flange extended. FIG. 3B shows a side view and FIG. 3C shows a top view of the capture device 300, which comprises the flange 310, the locking hinge 312, the wall 320 and the sifting piece 330. While a locking hinge is used to make the flange foldable, other means commonly practiced in the field may also be used to make a foldable flange. For example, when rigid plastic is used as the material for the flange, a folding line can be formed by partially removing the material underneath the folding line so that the remaining material becomes flexible enough to fold.

Figure 4A:
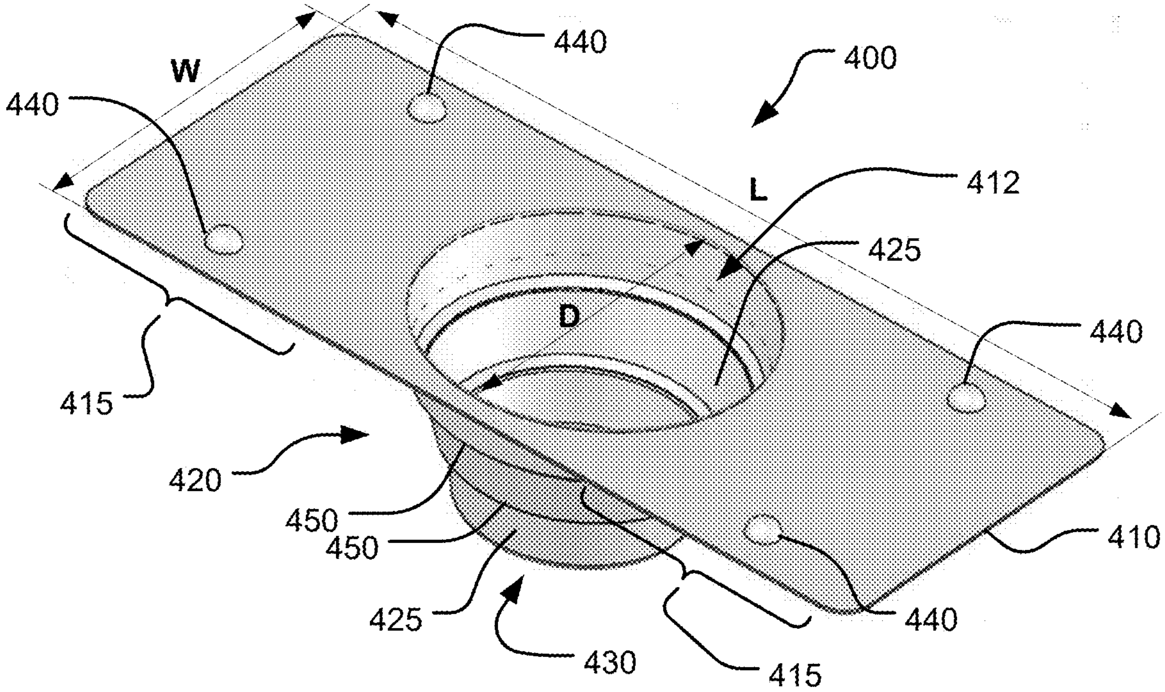
FIG. 4A-C illustrate an example of a collapsible pan for capsule retrieval according to one embodiment of the present invention, where
Figure 4B:
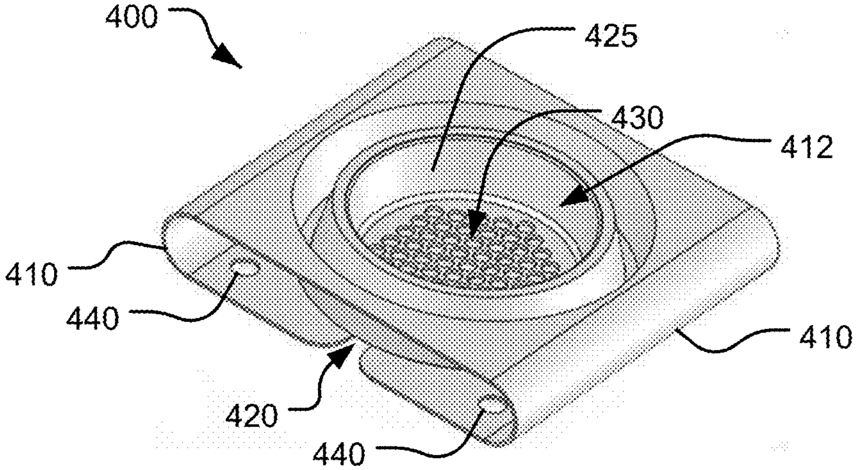
Figure 4C:
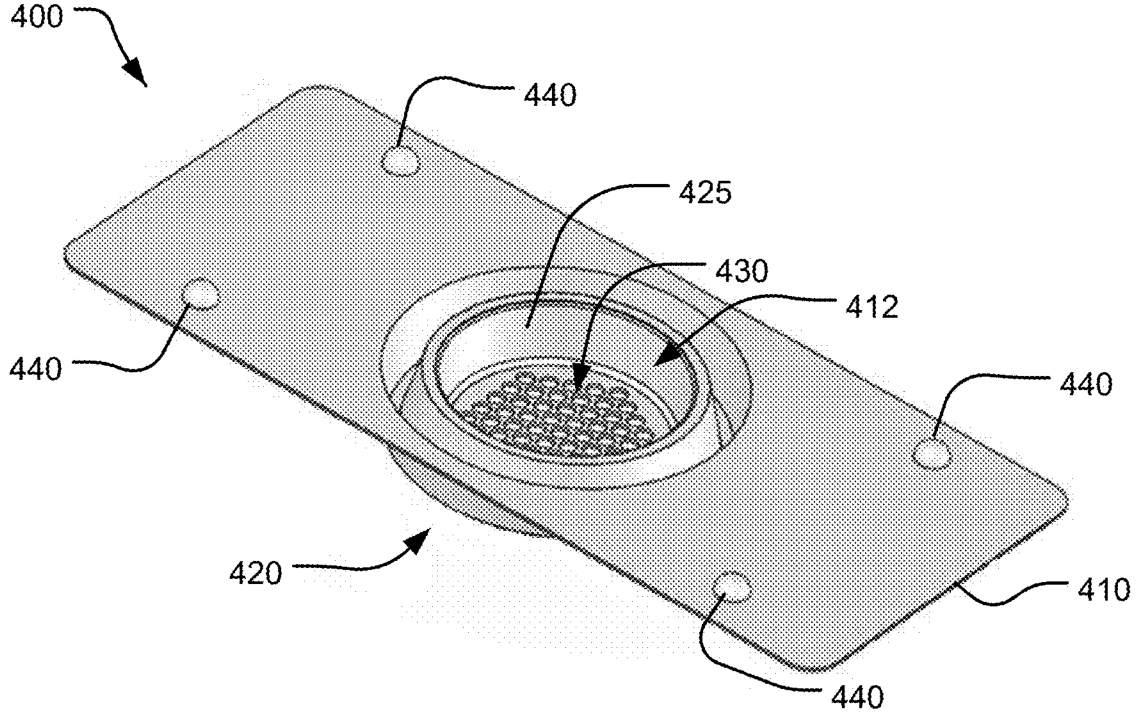

While the collapsible and foldable capture device 300 as shown in FIG. 3A can substantially save space, the foldable flange 310 is still rather large and may not be easily fit into some existing popular shipping boxed such as FedEx™ Pak box. Furthermore, the material for the wall 320 has to be thin, flexible and tall enough so that it can be easily collapsed to allow the flange 310 to be folded about the flange center as shown in FIG. 3A. In order to further improve the compactness for easy storage and shipping, a new collapsible retrieval pan is disclosed in the present invention. FIG. 4A-C illustrate an example of a collapsible pan 400 for capsule retrieval according to one embodiment of the present invention, where the pan comprises a flange 410, a collapsible cup 420 and the collapsible cup 420 comprises a wall portion 425 and a sifting piece 430 at the bottom. The center of the flange is a capture opening 412 intended to allow the feces to pass when the collection pan is deployed to retrieve the capsule. The flange is longer in one direction than the other. The Length L of the flange and the width W of the flange are indicated. FIG. 4A shows the pan in a state with the flange 410 and the collapsible cup 420 fully extended. The sifting piece 430 is not quite visible in this view. The portions of the flange extended from the capture opening 412 in the long direction are referred as wings 415 as shown in FIG. 4A. FIG. 4B shows the pan in a state with the flange 410 folded and the collapsible cup 420 collapsed. Most part of the sifting piece 430 is visible in this view. FIG. 4C shows the pan in a state with the flange 410 expanded and the collapsible cup 420 collapsed.

Figure 5A:
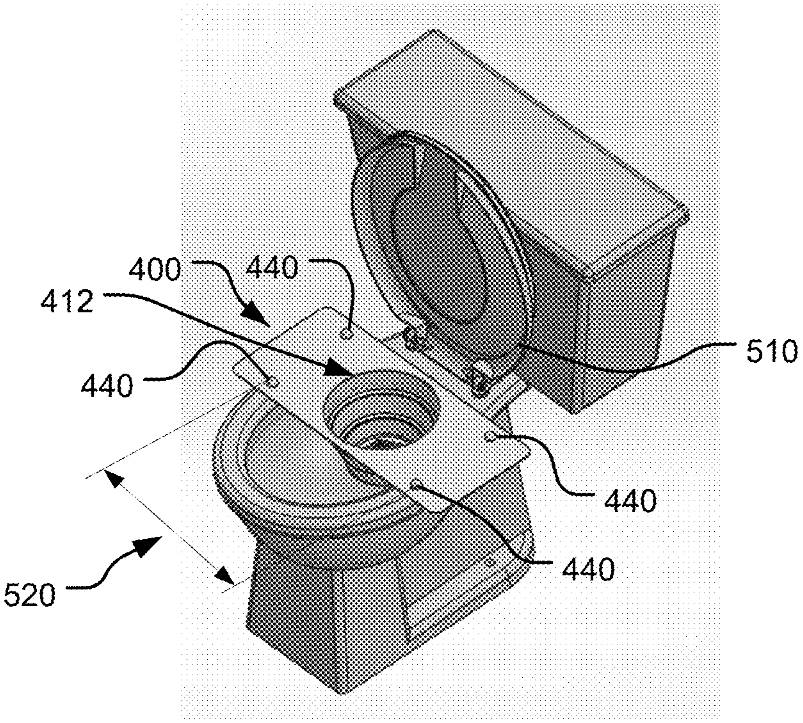
FIG. 5A illustrates a case of use where the flange is strong enough to support the pan hanging over the rim of the toilet bowl.
Figure 5B:
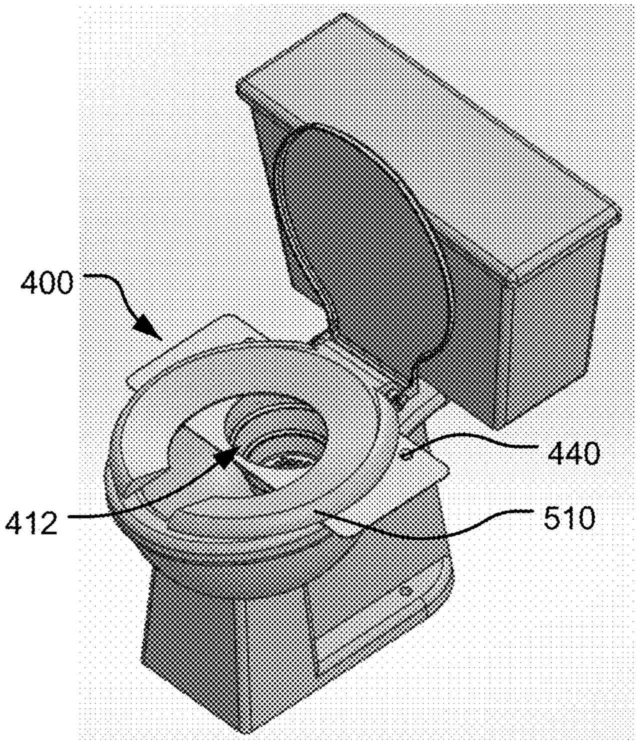
FIG. 5B shows the toilet seat is in a down position over the flange of the pan.

The pan in the state as shown in FIG. 4A is intended for deploying over the toilet bowl to retrieve the capsule to be excreted from a patient. The flange has to be strong enough to support the pan hanging over the rim of the toilet bowl as shown in FIG. 5A, where the toilet seat 510 is shown in an upright position. FIG. 5B shows the toilet seat 510 is shown in a down position over the flange 410 of the pan 400. Usually, there is a space between the seat and the toilet around 10 mm, where the space is created by spacers on the bottom side of the seat. Some seats have 4 spacers and the two spacers on the back can help to hold the pan 400 by placing pressure on the flange. Some seats have only 2 spacers and the two spacers are usually located near the front. In this case, the seat does not contact the flange. In order to help the pan stay in position, particularly after feces are dropped into the collapsible bowl, bumps are added to the flange. In one example, 4 bumps 440 are added to the flanges 410 as shown in FIG. 4A-B. The bump distance 520 between two corresponding bumps in the Length direction should match typical rim dimension as shown in FIG. 5A, where the two forward bumps match the rim dimension. In some cases, the two rear bumps match the rim dimension.

Figure 6:
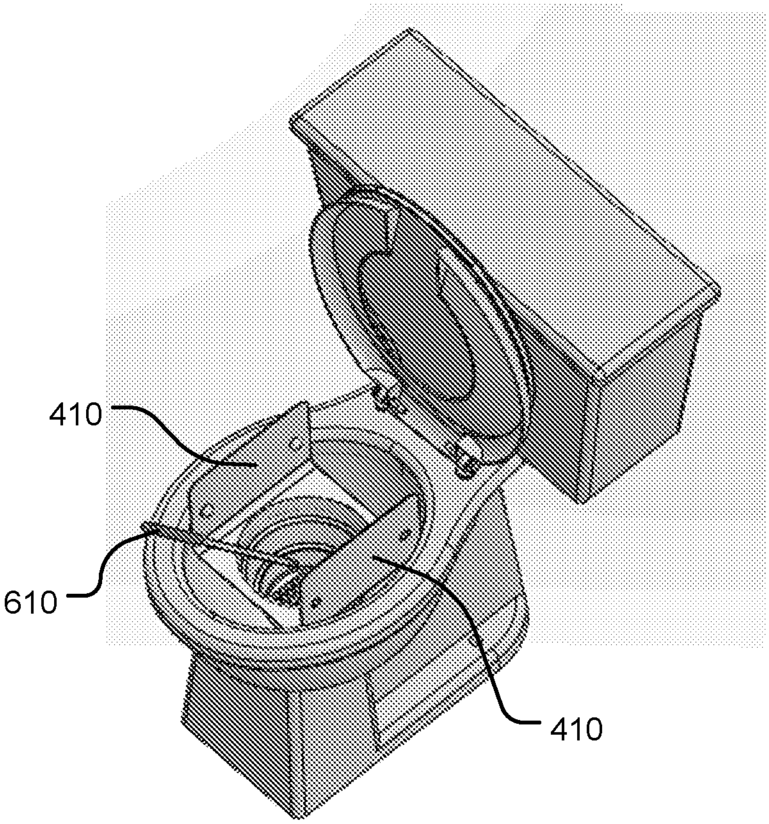
FIG. 6 illustrates a scenario where the flange can be grabbed by hands at the wings to lower the cup into toilet water.

After the capsule is excreted into the bowl, the capsule may be mixed with feces. A wand having a magnetic tip or other pick-up devices may be used to pick up the capsule from the cup. Water may be poured into the cup to separate the capsule from feces or other debris. Alternatively, a person can drop the pan into the toilet and pick up the capsule with the magnetic tip while shaking the pan in the toilet water to help find the capsule. FIG. 6 illustrates a scenario where the flange 410 can be grabbed at the wings by hands to lower the cup into toilet water. A wand with magnetic tip 610 is used to pick up the capsule. The flange can be made of rubber or rubber-like materials (e.g., silicone or Thermoplastic Polyurethane TPU) to provide the desired flexibility characteristics. The flange can be bended up at the portion toward the two edges in the Length direction.

The cup portion of the pan is designed to be collapsed by pressing down the flange around the cup opening area. Alternatively, the cup portion can be collapsed by pressing the cup bottom (i.e., the sifting piece) toward the cup opening. When the cup wall material is thin enough, the pressure from the cup opening and the cup bottom will cause the cup to collapse. In order to make the cup to collapses more smoothly, one or more folding lines or collapsing lines can be created on the cup wall. FIG. 4A shows an example of folding lines 450 on the cup wall. According to one embodiment of the present invention, the cup wall thickness is selected to be between 0.2 mm and 4 mm. If the cup wall is too thin, the cup shape may not be properly maintained and the sifting piece may not stay flat. On the other hand, if the cup wall is too thick, the cup may not be easily collapsed.

Flange should be longer than the rim distance where the flange will be over. The toilet usually has an oval shape and the rim distance varies depending on the location that the flange will cover. The flange length should fit most toilets being installed. According to one embodiment, the length is set to be between 200 mm and 500 mm. The flange width is set to be between 40 mm and 400 mm.

The thickness of the flange is another important design parameter. The thickness for the flange 410 according to embodiments of the present invention is set to between 1 mm and 6 mm. If the flange is too thin, it will not hold on to the toilet properly. On the other hand, it will not wrap or fold properly if it is too thick.

Figure 7:
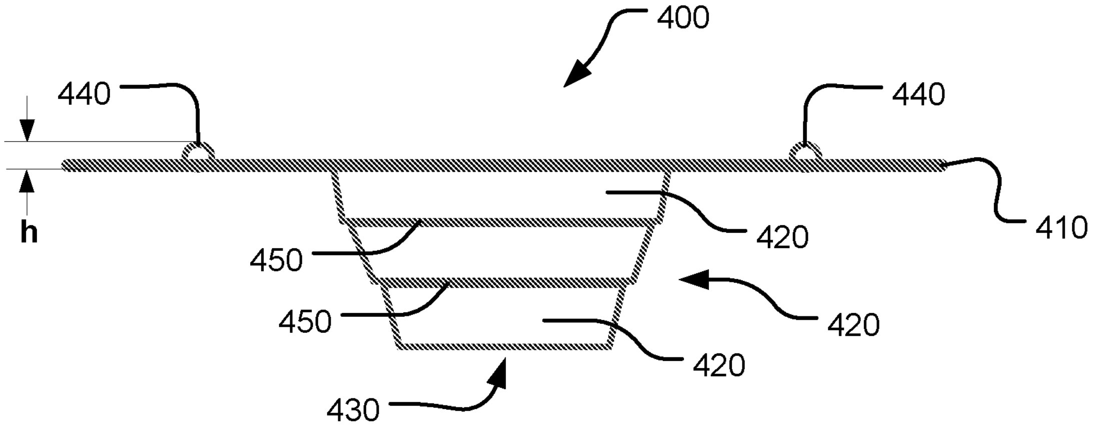
FIG. 7 shows the height h of the bumps including the thickness of the flange.

The bumps are intended to provide the needed space in case the no spacers are available to hold down the flange when the seat is lowered. The height h of the bump including the thickness of the flange is set to be between 4 mm to 12 mm as shown in FIG. 7.

The bottom of the cup comprises a sifting piece 430, which is formed by creating holes on the rubber-like material at the bottom. While the example in FIG. 4A-C corresponds to a round bottom, other shapes such as square or rectangle may also be used. However, the round bottom is a preferred embodiment since a round cup should make the collapsing movement more smooth. The holes on the bottom can be round, square, rectangle triangular, etc. The holes should be large enough to allow washed feces or debris to pass, but small enough to prevent the capsule to pass. Accordingly, in one embodiment of the present invention, the hole diameter is set to be between 0.2 mm and 12 mm when round holes are used.

The cup 420 in FIG. 4A-C has a larger diameter near the opening (indicated by D in FIG. 4A) and a smaller diameter near the bottom. This tapered design will make the collapsing action easier. The preferred cup diameter at the opening is set to between 40 mm and 400 mm according to one embodiment of the present invention. The flange width and the cup opening size D have to be considered jointly since the flange width W has to be larger than the cup opening. The preferred cup height at the extended state is set to between 100 mm and 300 mm according to one embodiment of the present invention.

In the disclosure, various embodiments and examples of the methods and structures mentioned above are described. It will be realized that this detailed description is illustrative only and is not intended to be in any way limiting. Other embodiments will readily suggest themselves to persons of ordinary skill in the art having the benefit of this disclosure.

The invention claimed is:

1. A collapsible pan for retrieving a capsule discharged from anus of a patient into a toilet bowl, comprising:
- a flange to adapt to a rim of the toilet bowl, wherein the flange comprises two wings and a capture opening for collecting feces, the flange having a top side and a bottom side and is longer in a length direction than a width direction, and the two wings are extended from the capture opening in a longer direction; and
- a collapsible cup joined to the flange around the capture opening, wherein the collapsible cup comprises a cup wall and a sifting part at a bottom of the collapsible cup, and wherein the sifting part comprises a plurality of holes to allow liquid or soft feces to pass while preventing the capsule to pass; and
- wherein the flange and the collapsible cup are made of rubber materials to provide a plurality of positions for the collapsible pan; and
- wherein the plurality of positions comprise:
- a first position corresponds to the flange laid flat with the two wings placed over the rim of the toilet bowl and with the bottom side facing toward the toilet bowl;
- a second position corresponds to the flange packed with the two wings folded respectively with the bottom side inward;
- a third position corresponds to the collapsible cup collapsed with the cup wall collapsed under pressure applied to top of the collapsible cup and the bottom of the collapsible cup; and
- a fourth position corresponds to the collapsible cup extended with the cup wall extended under a pull force applied between the bottom of the collapsible cup and the top of the collapsible cup.

2. The collapsible pan of claim 1, wherein the flange and the collapsible cup are made of a same material.

3. The collapsible pan of claim 1, wherein the flange comprises at least one bump on each of the two wings of the flange and distance between corresponding bumps of the two wings matches rim dimensions of the toilet bowl.

4. The collapsible pan of claim 3, wherein height of the bumps including thickness of the flange is between 4 mm to 12 mm.

5. The collapsible pan of claim 1, wherein the flange has a thickness between 1 mm and 6 mm.

6. The collapsible pan of claim 1, wherein the flange has a length between 200 mm and 500 mm.

7. The collapsible pan of claim 1, wherein the flange has a width between 40 mm and 400 mm.

8. The collapsible pan of claim 1, wherein the cup wall has a thickness between 0.2 mm and 4 mm.

9. The collapsible pan of claim 8, wherein the cup wall comprises one or more folding lines.

10. The collapsible pan of claim 1, wherein the plurality of holes have a shape of round, square, rectangle or triangular.

11. The collapsible pan of claim 10, wherein the plurality of holes are round with a diameter between 0.2 mm and 12 mm.

12. The collapsible pan of claim 1, wherein the capture opening is round with a diameter between 40 mm and 400 mm.

13. The collapsible pan of claim 1, wherein height of the collapsible cup at a fully extended state is between 10 mm and 300 mm.

* * * * *